United States Patent [19]

Clark

[11] 3,949,066

[45] Apr. 6, 1976

[54] ANTIPERSPIRANT AND DEODORANT COMPOSITION CONTAINING 2-ETHYL-1,3-HEXANE DIOL

[75] Inventor: Alan John Clark, Hanworth, England

[73] Assignee: Lever Brothers Company, New York, N.Y.

[22] Filed: Sept. 3, 1974

[21] Appl. No.: 502,701

Related U.S. Application Data

[63] Continuation of Ser. No. 323,007, Jan. 12, 1973, abandoned.

[30] Foreign Application Priority Data

Jan. 20, 1972 United Kingdom................. 2840/72

[52] U.S. Cl. ................................................ 424/47
[51] Int. Cl.² ...................... A61K 7/36; A61K 7/38
[58] Field of Search........................... 424/47, 65, 68

[56] References Cited
FOREIGN PATENTS OR APPLICATIONS

| | | |
|---|---|---|
| 1,159,685 | 7/1969 | United Kingdom................... 424/47 |
| 1,167,173 | 10/1969 | United Kingdom................... 424/47 |
| 987,301 | 3/1965 | United Kingdom................... 424/47 |

OTHER PUBLICATIONS

Lehne, Amer. Perfumer & Cosmetics, 10/1963, Vol. 73, pp. 103 to 107.

Lenthen, Amer. Perfumer & Cosmetics, 1966, Vol. 81, pp. 53 to 57.

*Primary Examiner*—Dale R. Ore
*Attorney, Agent, or Firm*—Arnold Grant

[57] ABSTRACT

An aerosol antiperspirant or deodorant composition containing, as a non-staining emollient substance or dispersing agent, 2-ethyl-1,3-hexane diol. The compositions may be solutions or suspensions and may contain germicides and antiperspirant agents.

A preferred form of the invention is a powder aerosol antiperspirant composition containing 2-ethyl-1,3-hexane diol as the dispersing agent. The following formulation is typical of such compositions:

| | % by weight |
|---|---|
| Aluminium chlorhydrate | 2 to 7.5 |
| Colloidal silica bulking agent | 0.05 to 0.75 |
| 2-ethyl-1,3-hexane diol | 1 to 5 |
| Germicide | up to 0.5 |
| Perfume | 0.01 to 2 |
| Aerosol propellant | balance |

8 Claims, No Drawings

ANTIPERSPIRANT AND DEODORANT COMPOSITION CONTAINING 2-ETHYL-1,3-HEXANE DIOL

This is a continuation, of application Ser. No. 323,007, filed Jan. 12, 1973 now abandoned.

This invention relates to antiperspirant or deodorant compositions.

Our co-pending cognate patent application Nos. 39690/70 and 50187/70 relates to antiperspirant or deodorant compositions in which the fatty emollient or dispersant substance conventionally used in such compositions is replaced at least in part by hexylene glycol (2-methyl-2,4-pentane diol). This results in a composition having a pleasant feel on the skin which has less of a tendency to stain clothing than an otherwise identical composition containing, for example, isopropyl myristate as the emollient or dispersing agent.

One of the problems which the use of hexylene glycol introduces is that of smell. Hexylene glycol itself has a smell which has to be masked before an acceptable antiperspirant or deodorant composition can be produced and also it tends to decompose to other substances having off-odours unless proper precautions are taken.

We have now discovered that when the fatty emollient substance conventionally used in antiperspirant and deodorant compositions is replaced by 2-ethyl-1,3-hexane diol, then not only is the feel on the skin improved and the tendency to stain clothing reduced to an extent similar to that achieved by using hexylene glycol, but also the tendency to produce off-odours is reduced.

Accordingly, the invention comprises a substantially non-staining aerosol antiperspirant or deodorant composition comprising an antiperspirant agent and/or germicide and 2-ethyl-1,3-hexane diol as an emollient substance or dispersant.

British Patent No. 1,159,685 mentions the substance 2-ethyl-1,3-hexane diol in connection with antiperspirants but the invention described is concerned with the preparation of soluble complexes of aluminium chloride and various diols of which 2-ethyl-1,3-hexane diol is one. Thus 2-ethyl-1,3-hexane diol itself is not present in the antiperspirant compositions described.

In its most preferred aspect the invention relates to an aerosol powder antiperspirant composition, that is to the general type of composition described in British Patent No. 1,167,173.

Accordingly, there is provided a substantially non-staining aerosol antiperspirant composition comprising a dispersion of a finely divided antiperspirant agent in a solution of 2-ethyl-1,3-hexane diol.

In general, the amount of 2-ethyl-1,3-hexane diol required in the compositions is from about 0.2 to 25% by weight, preferably 0.5 to 8 or even 10%, and most preferably 1 to 5% by weight. Rather less is required than when isopropyl myristate is used as the dispersing agent or emollient substance.

The physical form of the aerosol deodorant and antiperspirant compositions of the invention may be that of the so-called powder antiperspirant referred to above or it may be an aqueous, alcoholic or aqueous/alcoholic solution. In one form, an antiperspirant composition according to the invention comprises a $C_1$ to $C_4$ alcohol and an alcohol-soluble antiperspirant agent.

Any one of the large number of materials which have been proposed for use as astringent antiperspirant agents may be used in the compositions of this invention although, in the case of powder antiperspirant compositions, the antiperspirant agent should be capable of formulation as a dispersion in the antiperspirant medium. Thus any antiperspirant agent which is soluble in the commonly used aerosol propellants referred to below is excluded from use in these compositions since it will not be capable of formulation as a dispersion.

In general, the amount of the astringent metal salt required in the compositions of the invention will be from about 0.2 to 20%, preferably 0.2 to 10%, and most preferably 2 to 7% by weight of the composition.

Astringent metal salts, and in particular aluminium salts, are preferred as the antiperspirant agents of the invention. Most preferred is aluminium chlorhydrate. Grades of aluminium chlorhydrate which we have found particularly suitable in the compositions of the invention are those sold under the trade mark "Chlorhydrol" by the Reheis Chemical Company, a Division of the Armour Pharmaceutical Company, of 111 East Wacker Drive, PO Box 1022, Chicago, Ill. Detailed specifications of these grades are described in the booklet entitled "Chlorhydrol" published by the manufacturer in 1970.

Antiperspirant compositions of the solution type referred to above preferably contain an alcohol-soluble antiperspirant agent which is a complex salt of aluminium. Another alcohol-soluble antiperspirant agent which is particularly useful is zinc phenolsulphonate.

Powder aerosol antiperspirants commonly contain a bulking agent to help prevent irreversible settling of the finely-divided astringent metal salt and to ease its passage through the valve.

Any powder that is lower in bulk density than about 200 kilos per cubic meter may be used as the bulking agent, provided that it is insoluble in the liquid medium. Powders with a bulk density of 15 to 75 kilos per cubic meter are preferred.

The nature of the bulking agent is not critical to the invention. Examples of suitable bulking agents are finely-divided silicas, variously known as colloidal, fumed and pyrogenic silicas, and hydrophobic clays. Talc may also be used, as may grease-forming soaps such as aluminium stearate. Specific finely-divided silicas are: silica No. 22 referred to in U.S. Pat. No. 3,081,223, Santocel 54 (Trade Mark) manufactured by the Monsanto Company, St. Louis, Missouri; Cab-o-Sil M-5 (Trade Mark) a submicroscopic particulate silica prepared in a hot gas environment (1100°C) by the vapour phase hydrolysis of a silicon compound and available from the Cabot Corporation, Boston, Mass.; Bentone 34, a reaction product of montmorillonite and dimethyloctadecyl ammonium chloride, the latter constituting one third of the Bentone compound; and Aerosil 200, a pyrogenic silica manufactured by Deutsche Gold und Silberscheideanstalt of Frankfurt, West Germany. These bulking agents are preferably present in amounts of from 0.05 to 1.25%, more preferably 0.1 to 0.5% by weight.

The deodorant compositions will, and the antiperspirant compositions may contain a germicide. If a germicide is included then it will be in an amount of from about 0.01 to 0.05% by weight, depending on the degree of its germicidal activity.

If a germicide is to be used in the compositions of the invention, we prefer to use chlorhexidine, dichlorophene, and quaternary ammonium compounds such as cetyltrimethyl ammonium bromide.

The antiperspirant and deodorant compositions can contain perfumes in conventional amounts.

The compositions of this invention are dispensed from a conventional aerosol by means of a volatile aerosol propellant. In general the propellant or mixture thereof is chosen to produce a pressure of about 15 to 75, preferably about 25 to 45, and more preferably about 35 psig in the headspace of the can.

Typical of the halogenated hydrocarbons which can be used are the following compounds which have the following trade names: trichlorfluoromethane (Arcton 11), dichlorodifluoromethane (Arcton 12), dichlorofluoromethane (Arcton 113) and symmetrical dichlorotetrafluoroethane (Arcton 114).

Petroleum hydrocarbons such as propane and isopropane, n-butane and isopentane may also be used.

It may be desirable to include a surfactant in the aerosol powder antiperspirant compositions of the invention in order to assist with the dispersion of the finely divided antiperspirant agent in the liquid vehicle.

The surfactant should be both soluble in the antiperspirant vehicle (which consists essentially of a solution of 2-ethyl-1,3-hexane diol in an aerosol propellant, and chemically compatible with the other components of the composition. Once this requirement is satisfied the precise nature of the surfactant is not critical to the invention.

We prefer to use nonionic surfactants in the compositions of the invention although cationic and anionic surfactants can also be used. We have found the propylene glycol/propylene oxide condensates manufactured by the Wyandotte Chemical Company and sold under the Trade Mark "Pluronic" to be suitable nonionic surfactants. Amongst these Pluronic L62D and Pluronic L64 are preferred substances. Other nonionic surfactants which we have found to be suitable are polyoxyethylene lauryl ethers, such as that sold under the Trade Mark "Brij 30", polyoxyethylene cetyl ethers, such as that sold under the Trade Mark "Brij 52", water-soluble lanolins such as that sold under the Trade Mark "Solulan 98", polyoxyethylene stearates such as that sold under the Trade Mark "Myrj 52" and the mono-fatty acid esters of ethylene oxide/sorbitan condensates such as polyoxyethylene sorbitan monolaurates, polyoxyethylene sorbitan monopalmitates, polyoxyethylene sorbitan monostearates and polyoxyethylene sorbitan mono-oleates sold under the general Trade Mark "Tween".

Amongst those cationic surfactants which are suitable for use in the process and compositions of the invention are the quaternary ammonium salts such as cetyl trimethyl ammonium bromide, stearyl dimethyl benzyl ammonium chloride, Marinol (Trade Mark), "Quaterlan C" (Trade Mark) and "Morpan E" (Trade Mark).

An alkali metal alkyl ether sulphate, such as Empicol ESB-30 (Trade Mark), an aqueous solution of sodium lauryl ether sulphate containing an average of 2 ethylene oxide units per molecule is an example of a suitable anionic surfactant.

Typical amounts of surfactant in the powder antiperspirants are from about 0.01% to about 1.5% by weight of the final product, the preferred range being from about 0.02% to 0.2% or even 0.5% by weight. Expressed another way, the surfactant should preferably be present in the slurry at a level of about 0.3 to 3% or even 10% by weight.

The invention will be further described in the following Examples.

EXAMPLE 1

This example illustrates a typical process for preparing an aerosol powder antiperspirant composition containing aluminium chlorhydrate and a formulation of such an antiperspirant.

1 part by weight of chlorhexidine and 2 parts by weight of a surfactant are dissolved in 20 parts of 2-ethyl-1,3-hexane diol glycol together with the required amount of perfume. From 1 to 2 parts of Aerosil 200 are then suspended in the solution, and, after thorough mixing, 35 parts of finely divided aluminium chlorhydrate are added and mixed in to form a slurry.

A portion of the slurry formed in this way is dispensed into an aerosol unit and a propellant is added by the throughbutton filling method to form an antiperspirant according to the invention having the following composition:

|  | % by weight |
|---|---|
| Aluminium chlorhydrate | 3.1 |
| Aerosil 200 (a pyrogenic silica) | 0.1 |
| 2-ethyl-1,3-hexane diol | 2.0 |
| Chlorhexidine | 0.1 |
| Perfume | 0.4 |
| Arcton 11 (Trichlorofluoromethane) | 61.6 |
| Arcton 12 (Dichlorodifluoromethane) | 32.7 |
| Surfactant | 0.2 |
| "Arcton" is a Trade Mark. | |

It has been found that if a surfactant is incorporated in the slurry, as described above, it is possible to allow the slurry to stand for substantially longer periods of time prior to its being dispensed into an aerosol unit than is the case if the surfactant is omitted. We have found that if the surfactant is omitted the slurry forms a coherent mass in the bottom of the storage vessel within one or two days at the most.

Although in the above example of the process according to the invention the aerosol propellant is added to the slurry at a late stage by means of through-button filling, it will be understood that it may be added at earlier stages and by different methods. For example, if desired, propellants which are liquid at room temperature and pressure can be added to the preformed slurry prior to its being dispensed into aerosol cans.

EXAMPLE 2

This is a comparative example of a prior art aerosol powder antiperspirant composition containing isopropyl myristate.

|  | % by weight |
|---|---|
| Aluminium chlorhydrate | 3.5 |
| Chlorhexidine | 0.1 |
| Isopropyl myristate | 5.5 |
| Aerosil 200 | 0.1 |
| Perfume | 0.5 |
| Arcton propellants 12/11 (65:35) | 90.3 |

EXAMPLE 3

This example illustrates an aerosol powder antiperspirant composition not including a surfactant.

| | % by weight |
|---|---|
| Aluminium chlorhydrate | 3.5 |
| Aerosil 200 | 0.1 |
| 2-ethyl-1,3-hexane diol | 2.0 |
| Chlorhexidine | 0.1 |
| Perfume | 0.4 |
| Arcton 11 | 61.0 |
| Arcton 12 | 32.9 |

The advantages of the above composition are that it is not as easily transferred from the skin to the clothing as are compositions containing such fatty suspending agents as isopropyl myristate, and that even when it is transferred it is easily removed by washing. Both of these features result in the compositions of the invention having a much lower staining potential than compositions containing isopropyl myristate.

EXAMPLE 4

The following experiment shows that an aerosol antiperspirant of the formula in Example 1 is less easily transferred to clothing than is an antiperspirant of similar formulation containing 5.5% of isopropyl myristate and a correspondingly reduced amount of propellant instead of the 2% of 2-ethyl-1,3-hexane diol.

Each aerosol was sprayed from a standard distance and for 2 seconds onto the inner side of the forearm so that the antiperspirant composition covered a circular area of about 5 cm in diameter. The product was allowed 2 minutes to dry, after which time a weighed piece of cotton of about 5 cm in diameter was placed on the sprayed area and covered by 500 gram weight. After 15 minutes the weight was removed and the cotton was weighed to discover the amount of antiperspirant transferred from the skin.

The results were as follows:
| | |
|---|---|
| Aerosol containing isopropyl myristate | 4.0 mg. per. sq. cm. |
| Aerosol containing 2-ethyl-1,3-hexane diol | 0.5 mg. per sq. cm. |

This result shows the dramatic improvement in adhesion to the skin which is produced when the isopropyl myristate in an aerosol antiperspirant is replaced by 2-ethyl-1,3-hexane diol and we have found that the reduction in transferance is accompanied by a corresponding reduction in staining.

EXAMPLE 5

The following experiment shows that an aerosol antiperspirant of the formula in Example 1 produces a less pronounced stain on fabric than an antiperspirant of similar formulation containing 5.5% of isopropyl myristate and a correspondingly reduced amount of propellant instead of 2% 2-ethyl-1,3-hexane diol.

Each antiperspirant was sprayed onto a separate portion of the flexor surface of the forearm for 2 seconds so that the composition covered a circular area of about 5 cm in diameter. After a delay of 2 minutes to allow the composition to dry, the piece of pre-washed cotton was rubbed over each sprayed area using 5 strokes to give maximum pick-up of each composition. The pieces of fabric were then hand washed in 2 liters of water maintained at 40°C containing 10 grams of a domestic detergent powder. The washing process consisted of squeezing the impregnated cotton 10 times and then rinsing. The pieces were then dried in an oven maintained at 64°C for 30 minutes. Each antiperspirant was again sprayed onto the corresponding area of the forearm and the wipe/wash/dry procedure repeated. A total of 5 complete application/wash cycles was carried out for each antiperspirant, after which it was noted that the antiperspirant formulated with 2-ethyl-1,3-hexane diol produced no stain on the fabric whereas that formulated with isopropyl myristate produced a very noticeable oily stain.

A further advantage produced by the invention is that the percentage of 2-ethyl-1,3-hexane diol which is necessary to provide an aerosol antiperspirant having acceptable properties regarding suspension and flowability is much lower than that necessary in a similar composition containing isopropyl myristate. We have found that in the above example, a level of 2% of 2-ethyl-1,3-hexane diol is sufficient to perform the function of about 5.5% of isopropyl myristate.

EXAMPLE 6

This example illustrates an aerosol deodorant composition according to the invention.

| | % by weight |
|---|---|
| Industrial methylated spirit | 46.9 |
| 2-ethyl-1,3-hexane diol | 3.0 |
| Chlorhexidine | 0.1 |
| Propellants 12/11 (35:65) | 50.0 |

EXAMPLE 7

This example illustrates an aerosol antiperspirant composition according to the invention containing an alcohol-soluble antiperspirant agent.

| | % by weight |
|---|---|
| Rehydrol ASC (Trade Mark) | 8.0 |
| Industrial methylated spirit | 38.9 |
| 2-ethyl-1,3-hexane diol | 3.0 |
| Chlorhexidine | 0.1 |
| Propellant 114 | 20.0 |
| Propellant 12 | 30.0 |

Rehydrol ASC is an aluminium chlorhydroxide/propylene glycol complex manufactured by the Reheis Chemical Company.

It will be understood that the compositions of the invention may, if desired, contain small amounts of the conventional dispersing agents and emollients which produce staining although these amounts should not be so large as to detract from the overall non-staining character of the compositions. When a powder antiperspirant composition contains a small amount of isopropyl myristate we prefer it also to contain a polyalkylene glycol as described in our copending application No. 13827/70.

What is claimed is:

1. An improved substantially non-staining aerosol antiperspirant or deodorant composition comprising:
   a. an active ingredient selected from the group consisting of from about 0.2 to 20% by weight of antiperspirant agent, from about 0.01 to 0.05% by weight germicide and mixtures thereof;
   b. sufficient aerosol propellant to produce a pressure of about 15 to about 75 psig in the headspace of the aerosol container;

c. and wherein the improvement comprises from about 0.2 to 25% by weight of 2-ethyl-1,3 hexane diol as an emollient or dispersant; and the 2-ethyl-1,3 hexane diol being dissolved in the propellant to form a homogenous solution and the active ingredient being dissolved or dispersed in the solution.

2. A deodorant composition according to claim 1 comprising a germicide as the active ingredient in an amount of from about 0.01 to 0.5% by weight of the composition.

3. An antiperspirant or deodorant composition claim 1 comprising an astringent metal salt as the antiperspirant agent.

4. A composition according to claim 3 comprising a dispersion of the astringent metal salt in a finely-divided form in a solution of from 0.5 to about 10% by weight of the composition of 2-ethyl-1,3 hexane diol in an aerosol propellant.

5. A composition according to claim 4 wherein the astringent metal salt is an alcohol soluble complex of aluminum.

6. A composition according to claim 4 wherein the astringent metal salt is zinc phenol sulphonate.

7. A composition according to claim 5 further comprising from about 0.01 to about 1.5% by weight of a surfactant.

8. The composition according to claim 1 comprising
a. from about 2 to about 7.5% by weight of aluminum chlorhydrate;
b. from about 0.05 to about 0.75% by weight of silica bulking agent;
c. from about 0.5 to about 10% by weight of 2-ethyl-1,3-hexane diol;
d. from 0 to about 0.5% by weight of a germicide; and,
e. a perfume the balance consisting esentially of aerosol propellant.

* * * * *